US010827248B2

(12) United States Patent
Bacon et al.

(10) Patent No.: US 10,827,248 B2
(45) **Date of Patent: *Nov. 3, 2020**

(54) EARPHONE

(71) Applicant: Bose Corporation, Framingham, MA (US)

(72) Inventors: Cedrik Bacon, Ashland, MA (US); Keith Davidson, Brighton, MA (US); Daniel Collins, Waltham, MA (US); Liam Kelly, Milton, MA (US); Michael Zalisk, Arlington, MA (US)

(73) Assignee: Bose Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/284,727

(22) Filed: Feb. 25, 2019

(65) Prior Publication Data

US 2020/0275181 A1 Aug. 27, 2020

(51) Int. Cl.

*A61F 11/06* (2006.01)
*G10K 11/16* (2006.01)
*H03B 29/00* (2006.01)
*H04R 1/10* (2006.01)
*H04R 1/28* (2006.01)

(52) U.S. Cl.

CPC ......... *H04R 1/1016* (2013.01); *H04R 1/1075* (2013.01); *H04R 1/1083* (2013.01); *H04R 1/2888* (2013.01)

(58) Field of Classification Search

CPC .. H04R 1/1016; H04R 1/1075; H04R 1/1083; H04R 1/2888

See application file for complete search history.

(56) References Cited

U.S. PATENT DOCUMENTS

| | | | | |
|---|---|---|---|---|
| 6,597,792 B1 * | 7/2003 | Sapiejewski | H04R 1/1083 | 381/371 |
| 8,670,586 B1 * | 3/2014 | Boyle | H04R 1/1008 | 381/370 |
| 10,182,287 B2 * | 1/2019 | Struzik | H04R 1/2873 | |
| 2012/0039500 A1 * | 2/2012 | Silvestri | H04R 1/1016 | 381/380 |
| 2014/0363040 A1 * | 12/2014 | Silvestri | H04R 1/2888 | 381/380 |
| 2015/0264467 A1 * | 9/2015 | Annunziato | H04R 1/1058 | 381/380 |
| 2015/0382100 A1 * | 12/2015 | Azmi | H04R 1/1091 | 381/380 |
| 2016/0150310 A1 * | 5/2016 | Bakalos | H04R 1/1083 | 381/372 |
| 2016/0219360 A1 * | 7/2016 | Zhao | H04R 1/1016 | |
| 2017/0006373 A1 * | 1/2017 | Bruss | H04R 1/1075 | |
| 2017/0223443 A1 * | 8/2017 | Silvestri | H04R 1/1016 | |
| 2018/0041828 A1 * | 2/2018 | Sibbald | G10K 11/178 | |

* cited by examiner

*Primary Examiner* — Simon King

(74) *Attorney, Agent, or Firm* — Brian M. Dingman; Dingman IP Law, PC

(57) ABSTRACT

An earphone with a first acoustic cavity, an electro-acoustic transducer configured to deliver acoustic energy into the first acoustic cavity, and a port that acoustically couples the first acoustic cavity to a different volume, wherein the port comprises a series of through-holes that are open to the first acoustic cavity and the different volume.

18 Claims, 6 Drawing Sheets

EARPHONE

BACKGROUND

This disclosure relates to an earphone.

Earphones may have one or more ports. The ports can be used, for example, to tune the acoustic performance of the earphone or deliver sound into the ear canal. Ports can comprise an opening with a mesh material covering the opening.

SUMMARY

All examples and features mentioned below can be combined in any technically possible way.

In one aspect, an earphone includes a first acoustic cavity, an electro-acoustic transducer configured to deliver acoustic energy into the first acoustic cavity, and a port that acoustically couples the first acoustic cavity to a different volume, wherein the port comprises a series of through-holes that are open to the first acoustic cavity and the different volume.

Examples may include one of the above and/or below features, or any combination thereof. The earphone may further include a second acoustic cavity, wherein the electro-acoustic transducer is configured to deliver acoustic energy into the first and second acoustic cavities. The port may directly acoustically couple the first and second acoustic cavities. The earphone may further include a frame that supports the transducer. The port may be integrated into the frame. The frame may comprise an annular seat for the transducer, and an integral extension that comprises the port.

Examples may include one of the above and/or below features, or any combination thereof. The port may comprise an integral structure that comprises the series of through-holes. The port may comprise an acoustically resistive element. The port may comprise an acoustically reactive element. The port may comprise a tube. The port may acoustically couple the first acoustic cavity to an environment external to the earphone. The port may comprise a nozzle that is configured to directly deliver acoustic energy into an ear canal.

Examples may include one of the above and/or below features, or any combination thereof. The series of through-holes may comprise a moisture-resistant element. The series of through-holes can be created by molding, machining, laser drilling, chemical etching, electrical discharge machining, or electroforming, for example.

Examples may include one of the above and/or below features, or any combination thereof. The through-holes of the series of through-holes may be identical. The through-holes of the series of through-holes may have lengths and diameters, and the diameters of at least some of the through-holes may vary along their lengths. The through-holes of the series of through-holes may have lengths, and at least some of the through-holes may be tapered along their lengths. The through-holes of the series of through-holes may have first openings that are open to the first acoustic cavity and second openings that are open to the different volume. Some of the through holes may have larger first openings than second openings, and some of the through holes may have smaller first openings than second openings. The through holes may have sidewalls, and the sidewalls of adjacent through-holes may be parallel.

In another aspect, an earphone includes a front acoustic cavity, a rear acoustic cavity, an electro-acoustic transducer configured to deliver acoustic energy into the front and rear acoustic cavities, and an internal port that directly acoustically couples the front and rear acoustic cavities, wherein the port comprises a series of adjacent molded through-holes.

Examples may include one of the above and/or below features, or any combination thereof. The earphone may further include a frame that supports the transducer. The port may be integrated into the frame. The frame may comprise an annular seat for the transducer, and an integral extension that comprises the port. The earphone may further include a nozzle that is configured to directly deliver acoustic energy from the front cavity into an ear canal, and a moisture-resistant element in the nozzle and that comprises the through-holes. The earphone may further include an external port that acoustically couples the rear cavity to an environment external to the earphone and comprises an opening that comprises a series of adjacent molded through-holes.

DETAILED DESCRIPTION

Earphones often use mesh material to provide a desired acoustic resistance in one or more ports of the earphone. Mesh materials can also be used to cover port openings so as to inhibit moisture or particulate ingression without substantial acoustic resistance. The mesh materials are typically applied in a post-molding operation, which increases earbud production costs and can lead to inhibited performance due to variation in performance between products. The mesh material can be replaced with an acoustically or environmentally resistive element that comprises a structure with a series of micro-perforations (i.e., through-holes) that allow air flow through the structure. The micro-perforations can be integrally formed during injection molding of the part of the earphone that comprises the port. This does away with the post-molding operation and leads to greater earphone operational uniformity. In addition, this dramatically simplifies assembly of the earphone.

An earphone or a headphone refers to a device that typically fits around, on, in, or near an ear and that radiates acoustic energy into or towards the ear canal. Headphones and earphones are sometimes referred to as earpieces, headsets, earbuds, or sport headphones, and can be wired or wireless. An earphone includes an electro-acoustic transducer to transduce audio signals to acoustic energy. The electro-acoustic transducer may be housed in an earcup, earbud, or other housing. Some of the figures and descriptions following show a single earphone device. An earphone may be a single stand-alone unit or one of a pair of earphones (each including at least one electro-acoustic transducer), one for each ear. An earphone may be connected mechanically to another earphone, for example by a headband and/or by leads that conduct audio signals to an electro-acoustic transducer in the headphone. An earphone may include components for wirelessly receiving audio signals. An earphone may include components of an active noise reduction (ANR) system. Earphones may also include other functionality, such as a microphone. An earphone may also be an open-ear device that includes an electro-acoustic transducer to radiate acoustic energy towards the ear canal while leaving the ear open to its environment and surroundings.

In an around-the-ear, on-the-ear, or off-the-ear earphone, the earphone may include a headband and at least one housing that is arranged to sit on or over or proximate an ear of the user. The headband can be collapsible or foldable, and can be made of multiple parts. Some headbands include a slider, which may be positioned internal to the headband, that provides for any desired translation of the housing. Some earphones include a yoke pivotably mounted to the headband, with the housing pivotably mounted to the yoke, to provide for any desired rotation of the housing.

Figure 1:
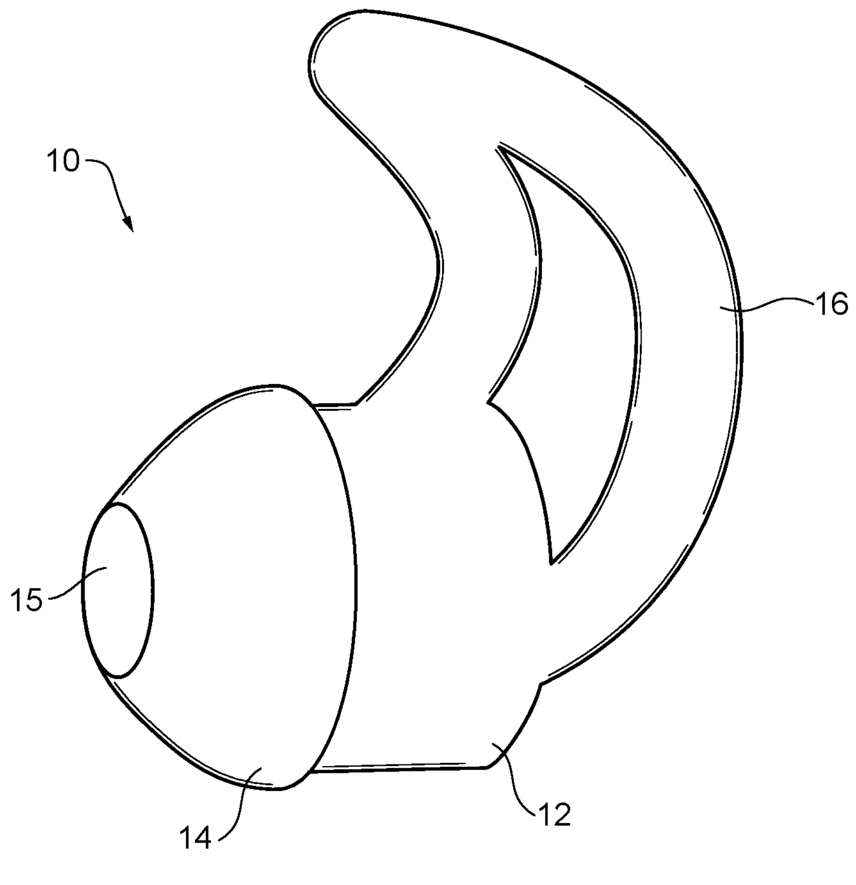
FIG. 1 is perspective view of an earphone.

FIG. 1 is a perspective view of in-ear headphone, earphone, or earbud 10. Earphone 10 includes body 12 that houses the active components of the earbud. Ear tip portion 14 is coupled to body 12 and is pliable so that it can be inserted into at least the entrance of the user's ear canal. Sound is delivered through opening 15. Retaining loop 16 is constructed and arranged to be positioned in the outer ear, for example in the antihelix, to help retain the earbud in the ear. Earphones and earbuds are well known in the field (e.g., as disclosed in U.S. Pat. Nos. 9,854,345 and 8,989,427, the disclosures of which are incorporated herein by reference in their entirety and for all purposes), and so certain details of the earbud are not further described herein. An earbud is an example of an earphone according to this disclosure, but is not limiting of the scope, as earphones can also be located on or over the ear, or even on the head near the ear.

Figure 2:
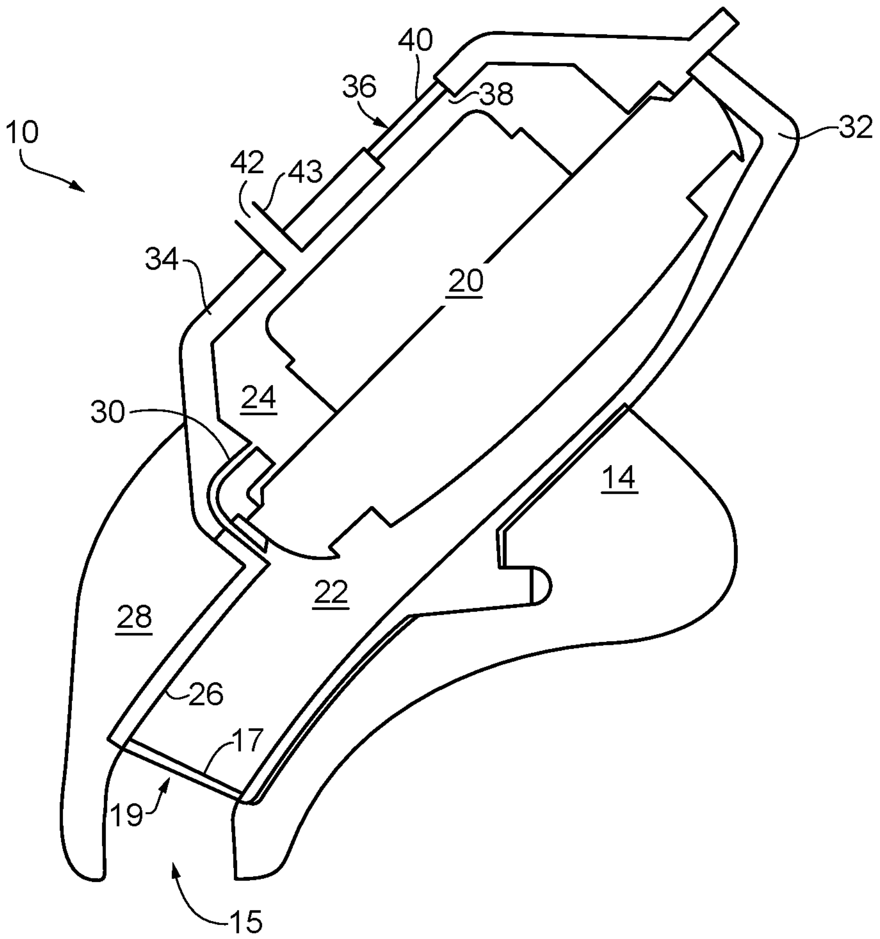
FIG. 2 is a cross-sectional view of selected parts of an earphone.

As shown in FIG. 2, earphone 10 includes a rear acoustic chamber 24 and a front acoustic chamber 22 defined by shells 34 and 32 of the housing, respectively, on either side of an electro-acoustic transducer 20. Note that in the drawings and the following description, non-limiting values of some variables are used. These values represent specific non-limiting examples, it being understood that the disclosure is in no way limited by these examples. In some examples, a 14.8 mm or 9.7 mm diameter electro-acoustic transducer can be used. Other sizes and types of electro-acoustic transducers could be used depending, for example, on the desired frequency response and performance of the earphone. The electro-acoustic transducer 20 separates the front and rear acoustic chambers 22 and 24. The shell 32 of the housing extends the front chamber 22 via nozzle 26 to at least the entrance to the ear canal 28, and in some examples into the ear canal 28, through the ear tip portion 14 and ends at an opening 15 that may include element 17 that can be an acoustic resistance element or a moisture or particulate barrier element, for example. Element 17 may comprise a barrier to air flow (e.g., a structure, wall or membrane) with a series of small spaced through-holes (not shown). The through-holes allow air flow through the barrier and may be designed to present a certain acoustical or environmental resistance. In some examples, element 17 is located within nozzle 26 rather than at the end, as illustrated. In some examples, element 17 may comprise a perforated cap that fits over the end of nozzle 26.

An acoustic resistance element dissipates a proportion of acoustic energy that impinges on or passes through it. In other examples, no resistance element is included, but a screen (with low acoustic resistance) may be used in its place to prevent or inhibit moisture or debris from entering the front chamber 22. The screen can be but need not be created by a series of through-holes in a structure such as a thin wall. In this non-limiting example, the front chamber 22 does not have a pressure equalization (PEQ) port to connect the chamber 22 to an environment external to the earphone.

Instead, a PEQ port 30 acoustically couples the front acoustic chamber 22 and the rear acoustic chamber 24. The port 30 serves to relieve air pressure that could be built up within the ear canal 28 and front chamber 22 when (a) the earphone 10 is inserted into or removed from the ear canal, (b) a person wearing the earphone 10 experiences shock or vibration, or (c) the earphone 10 is struck or repositioned while being worn. The port 30 preferably has a diameter of between about 0.25 mm to about 3 mm. The port 30 preferably has a length of between about 0.25 mm to about 10 mm. Port 30 can have an acoustic resistance element or a screen (not shown) if desired, to alter the impedance of the port or provide environmental protection.

The amount of passive noise reduction that can be provided by a ported earphone is often limited by the acoustic impedance through the ports, and the air volume in front of or behind the electrodynamic transducer. Generally, more passive noise reduction is preferable. However, certain port geometry is often needed in order to have proper system performance. Ports can be used to improve acoustic output, equalize audio response, and provide a venting path during overpressure events. Impedance may be changed in a number of ways, some of which are related. Impedance is frequency dependent, and it may be preferable to increase impedance over a range of frequencies and/or reduce the impedance at another range of frequencies. The impedance has two components: a resistive component (DC flow resistance) and a reactive either mass component $j\omega$ or compliance $1/j\omega$. The total impedance can be calculated at a specific frequency of interest by determining the magnitude or absolute value of the acoustic impedance $|z|$. The port 30 can have a desired absolute value $|z|$ acoustic impedance at different frequencies.

The primary purpose of the port 30 is to avoid an over-pressure condition when, e.g., the earphone 10 is inserted into or removed from the user's ear 10, or during use of the earphone. Pressure built up in the front acoustic chamber 22 escapes to the rear acoustic chamber 24 via the port 30, and from there to the environment via back cavity ports 42 and 36, mainly the mass port 42 (discussed in more detail below). Additionally, the port 30 can be used to provide a tuned amount of leakage that acts in parallel with other leakage that may be present. This helps to standardize response across individuals. Adding the port 30 makes a tradeoff between some loss in low frequency output and more repeatable overall performance. The port 30 provides substantially the same passive attenuation as completely blocking a typical front chamber PEQ port with similar architecture. The port 30 in series with the rear cavity ports 42 and 36 provides a higher impedance venting leak path compared with using a traditional front chamber PEQ instead of the port 30. Surprisingly, however, it was found that this higher impedance results in a more linear behavior during pressure equalization events which reduces the negative impact of the higher impedance.

The rear chamber 24 is sealed around the back side of the electro-acoustic transducer 20 by the shell 34 except that the rear chamber 24 includes one or both of a reactive element, such as a port (also referred to as a mass port) 42, and a resistive element, which may also be formed as a port 36. The reactive element 42 and the resistive element 36 acoustically couple the rear acoustic chamber 24 with an environment external to the earphone, thereby relieving the air pressure mentioned above. U.S. Pat. No. 6,831,984 describes the use of parallel reactive and resistive ports in a headphone device, and is incorporated herein by reference. Although we refer to ports as reactive or resistive, in practice any port will have both reactive and resistive effects. The term used to describe a given port indicates which effect is dominant. A reactive port like the port 42 is, for example, a tube-shaped opening in what may otherwise be a sealed acoustic chamber, in this case rear chamber 24. A resistive element like the port 36 can be, for example, a small opening 38 in the wall 34 of acoustic chamber 24, covered by a material 40 that provides an acoustical resistance, for example, a wire or fabric screen (mesh) that allows some air and acoustic energy to pass through the wall of the chamber, or a blocking structure such as a wall or membrane with a series of small through-holes as described herein.

The reactive element 42 can have an absolute value acoustic impedance |z| in a desired range, which may differ at different frequencies. The resistive element 36 may have a desired acoustic impedance. The reactive element 42 preferably has a diameter of between about 0.5 mm to about 2 mm, and more preferably has a diameter of about 1 mm. The reactive element 42 preferably has a length of between about 5 mm to about 25 mm, and more preferably has a length of about 15 mm. The resistive element 36 preferably has a diameter of about 1.7 mm and a length of preferably about 1 mm. Element 36 may be covered with a 260 rayls or 160 rayls resistive material (e.g. woven cloth) 40, or may achieve an equivalent resistance with properly sized and shaped through-holes in a wall of desired thickness that spans the opening. These dimensions provide both the acoustic properties desired of the reactive port 42, and an escape path for the pressure built up in the front chamber 22 and transferred to the rear chamber 24 by the port 30. The ports 42 and 36 provide porting from the rear acoustic chamber 24 to an environment external to the earphone. Furthermore, in order to receive a meaningful benefit in terms of passive attenuation when using a front to back port 30 in a ported system, the ratio of the impedance of the ports 42 and 36 to the impedance of the port 30 is preferably greater than 0.25 and more preferably around 1.6 at 1 kHz.

For an active noise reduction (ANR) earphone two functions (of many) of the ports 30, 42 and 36 are to increase the output of the system (improves active noise reduction) and provide pressure equalization. In addition, it is desirable to maximize the impedance of these ports at frequencies that can improve the total system noise reduction. At certain frequencies (e.g., at low frequency) it may be preferable for the impedance to allow for venting pressure or increasing low frequency output, and at certain other frequencies (e.g., at 1 kHz) it may be preferable for the impedance to be different in order to maximize passive noise reduction. Ports allow this to occur as they can have a different resistive DC component from the reactive frequency dependent component depending upon their design.

Any one or more of the ear tip portion 14, cavities 24 and 22, electro-acoustic transducer 20, screen 17, port 30, and elements 42 and 36, can have acoustic properties that may affect the performance of the earphone 10. These properties may be adjusted to achieve a desired frequency response for the earphone. Additional elements, such as active or passive equalization circuitry, may also be used to adjust the frequency response. The rear chamber 24 preferably has a volume of between about 0.1 $cm^3$ to about 3.0 $cm^3$, and more preferably has a volume of about 0.5 $cm^3$ (this volume includes a volume behind a diaphragm of the electro-acoustic transducer 20 (inside the transducer), but does not include a volume occupied by metal, pcb, plastic or solder). Excluding the electro-acoustic transducer, the front chamber 22 preferably has a volume of between about 0.05 $cm^3$ to about 3 $cm^3$, and more preferably has a volume of about 0.25 $cm^3$.

The reactive port 42 resonates with the back chamber volume. In some examples, the reactive port 42 and the resistive port 36 provide acoustical reactance and acoustical resistance in parallel, meaning that they each independently couple the rear chamber 24 to free space. In contrast, reactance and resistance can be provided in series in a single pathway, for example, by placing a resistive element such as a wire mesh screen inside the tube of a reactive port. In some examples, a parallel resistive port is made from an 80x700 Dutch twill wire cloth, for example, that available from Cleveland Wire of Cleveland, Ohio, and has a diameter of about 1.7 mm. Parallel reactive and resistive elements, embodied as a parallel reactive port and resistive port, provides increased low frequency response compared to an example using a series reactive and resistive elements. The parallel resistance does not substantially attenuate the low frequency output while the series resistance does. Using a small rear cavity with parallel ports allows the earphone to have improved low frequency output and a desired balance between low frequency and high frequency output.

Some or all of the elements described above can be used in combination to achieve a particular frequency response (non-electronically). In some examples, additional frequency response shaping may be used to further tune sound reproduction of the earphones. One way to accomplish this is with passive electrical equalization using circuitry (not shown). Such circuitry can be housed in-line with the earphones or within the housing of the earphones, for example. If active noise reduction circuitry or wireless audio circuitry is present, such powered circuits may be used to provide active equalization.

Any one or more of the ports (e.g., ports 19, 30, 36, and/or 42) can comprise an opening that comprises an element comprising a structure (such as a wall or membrane) that spans the opening and includes a series of through-holes, as described herein. The through-holes can be created in any presently known or future developed manner. In one instance, the openings are created when the port is created, e.g., by injection molding. Openings can be created in injection molding with pins or other structures in the mold tool that create voids in the molded part. The openings can also be created by a post-molding operation. Examples of manners in which openings can be created include but are not limited to molding, machining, laser drilling, chemical etching, electrical discharge machining, and electroforming.

The structure with the through-holes can span the port opening at any location along the length of the port, up to and including either surface at the ends of the port. This structure (typically but not necessarily including the through-holes) can be made by injection molding. Injection molding is well known in the field. Through-holes can be created by properly placed structures (such as pins) in the mold tool and in manners well known in the field. The port and its unitary structure with through-holes can be formed (molded) as a separate part that is then coupled to other earphone structures (such as the housing) or it can be integrally formed as part of an injection-molded housing, or as a portion of the housing. For example, structure 40 that comprises a plurality of through-holes can be molded as part of shell 34. Also, a structure 40 could likewise be molded in a frame or other portion of an electro-acoustic transducer as part of front-to-back PEQ 30.

Molding of a structure with openings into a port of an earphone can substantially improve the earphone and simplify its fabrication. The openings may be created by the injection mold tool that is used to produce various parts of the earbud (e.g., shells 32 and 34), including the opening of ports 30, 36, and 42. Accordingly, there are no extra steps needed in order to create the resistive element that comprises a structure with openings. This is in contrast to the current fabrication approaches that involve post-molding operations such as adhering a mesh material into a port (e.g., using a pressure sensitive adhesive (PSA)) or heat staking a mesh material into a port (which involves softening a thermoplastic port material post-molding and embedding the mesh material into the softened plastic, which then hardens and encapsulates the mesh). Creating the acoustically-resistive or environmentally-resistive element by injection molding can thus save time and effort during earbud fabrication. Also, molding is reliable in its ability to properly form the openings while not affecting the material that creates the port opening. This leads to less chance of acoustic leakage or water leakage compared to the use of PSA, which can lead to incomplete adhesion and thus leakage, or even to the failure of the adhesive joint.

Although benefits in ease of assembly are maximized when the port opening is integral to a larger structure, in its simplest form the port may be a stand-alone injection molded component comprising just a frame of injection molded plastic with the openings/through-holes. Adhering such a rigid plastic frame onto surrounding structure is a far less sensitive process than capturing the edges of a mesh. This type of variation may be used in cases where the plastic component containing the port opening is produced by sufficiently complex molding and tooling such that molding of the larger structure is no longer feasible. Also, with this approach the port structure itself and the port opening are left intact and untouched. In contrast, the PSA in an adhesive joint and the softened and re-hardened plastic in a heat-staked joint can partially block the port and have an effect on the acoustic performance of the port. Injection molding is also a repeatable, mostly or fully-automated process, leading to less variation between products. The product consistency also allows acoustic earphone considerations, such as active noise reduction, to be implemented more aggressively than might be the case where there could be more variation product-to-product.

The structure and the series of openings through the structure can be designed to create an acoustic resistance and/or it can be used for environmental protection purposes, for example to inhibit the passage of moisture and/or particles.

Figure 3:
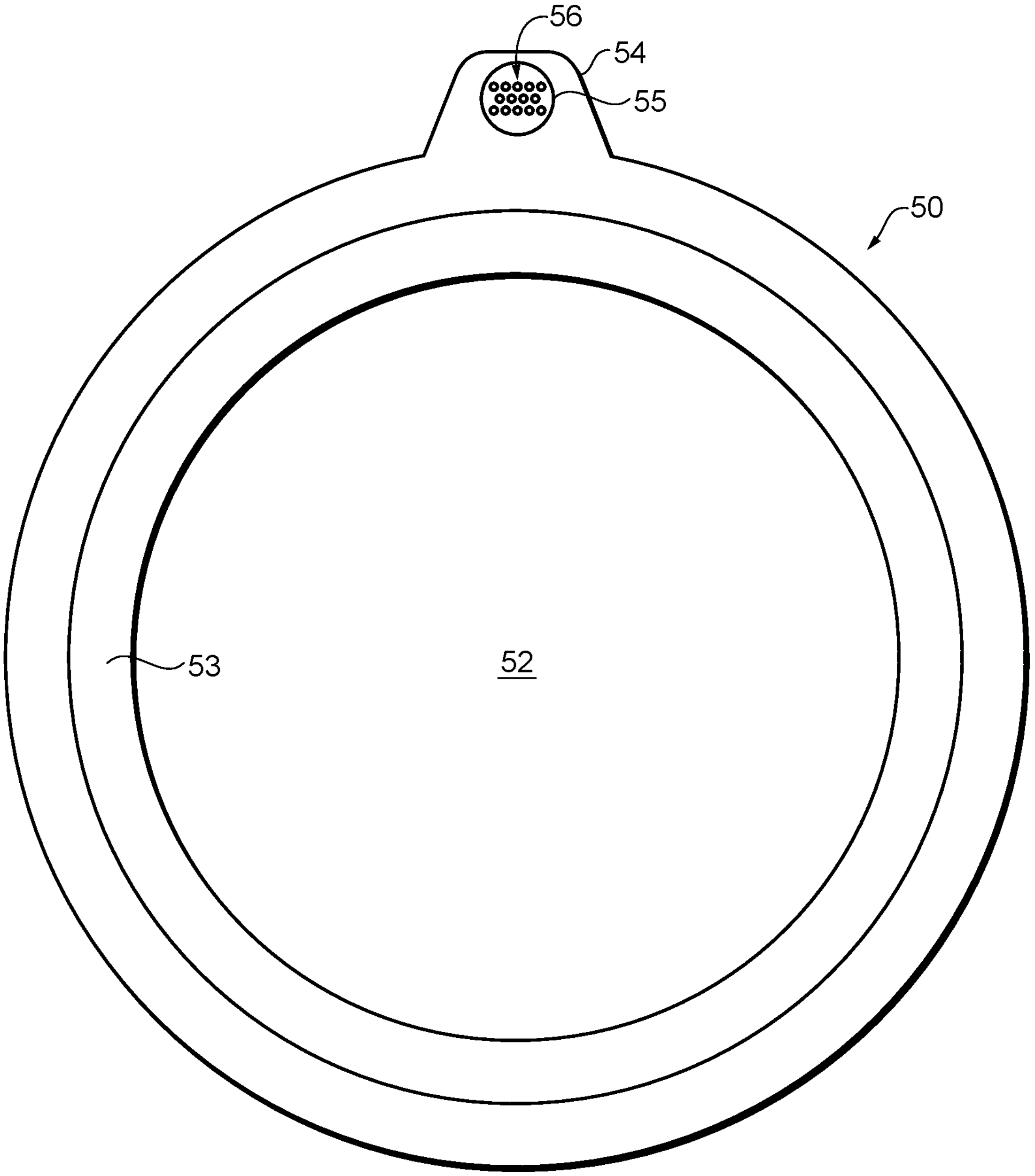
FIG. 3 is a top view of a frame for the electro-acoustic transducer of an earphone.

In one specific, non-limiting implementation of an earphone, the electro-acoustic transducer can be mounted on open frame 50, FIG. 3. Frame 50 is only one non-limiting example of how a PEQ port with an integral molded resistive element can be accomplished. For example, the PEQ port with integral-molded resistive element could reside in earphone structures other than the frame, and/or the transducer could be mounted in the housing without the use of a mounting frame. Frame 50 can be an integral molded structure that comprises annular seat 53 on which the transducer can sit, opening 52 to accommodate the diaphragm and other structures of the transducer, and extension 54 with through-hole 55 in which structure with through-holes 56 is created during molding of frame 50. Hole 55 with integral structure 56 forms a port, e.g., a PEQ port that directly acoustically connects the front and rear acoustic cavities of the transducer. Frame 50 can be carried inside the earphone housing (not shown) as would be apparent to those skilled in the technical field.

Figure 4:
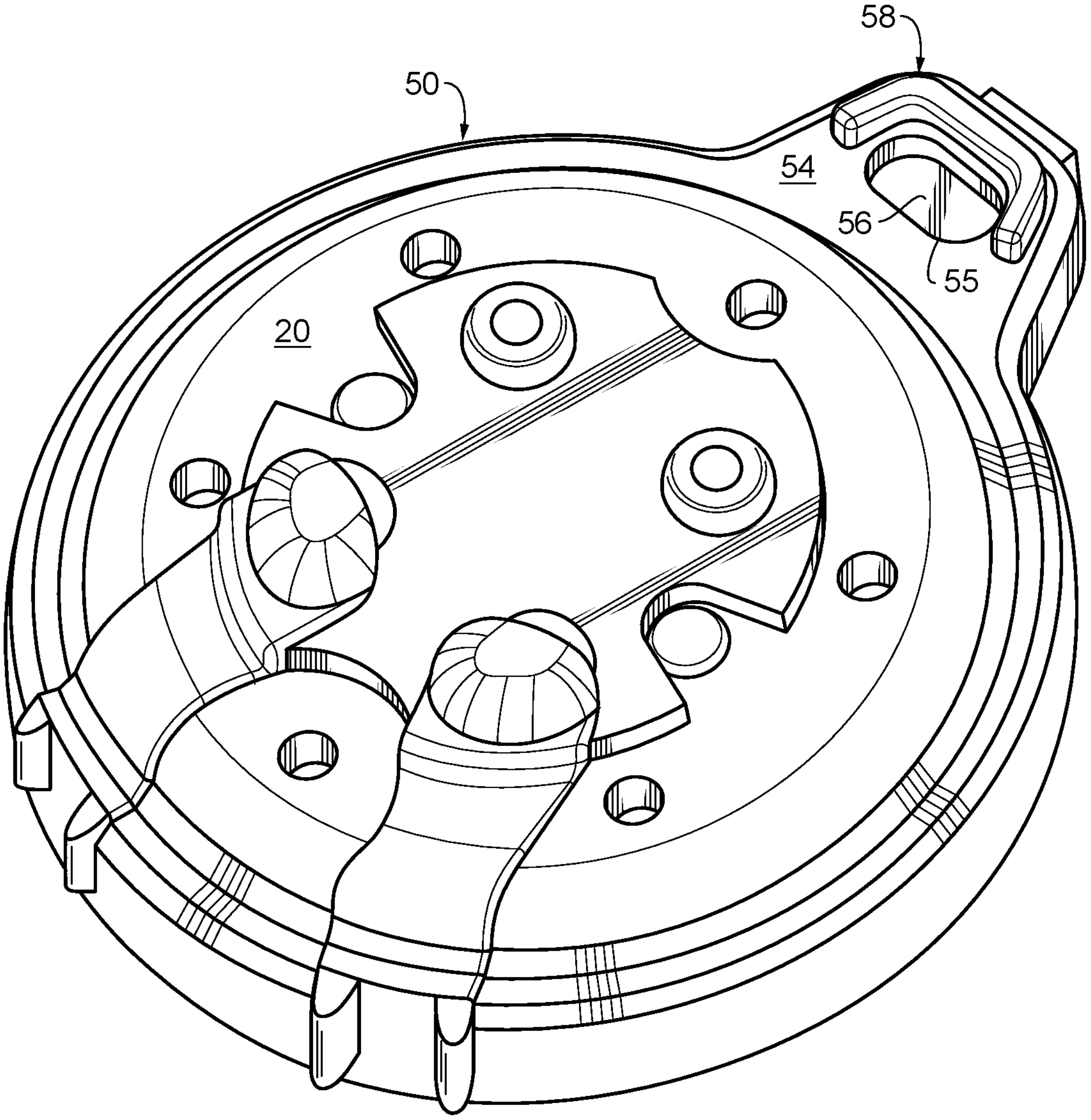
FIG. 4 is a rear perspective view of the frame of FIG. 3 with the transducer mounted in the frame.

FIG. 4 is a rear perspective view of frame 50 and transducer 20 mounted in the frame. In this non-limiting example, a ridge or protrusion 58 is located or placed on top of extension 54 surrounding part of through-hole 55. Ridge 58 can be an integral portion of the molded structure, or can be added separately. A purpose of ridge 58 is to inhibit any adhesive used to mount transducer 20 in frame 50 (or used to mount frame 50 in the housing) from being pushed into hole 55 during assembly, as this could cause unwanted and uncontrolled changes to the performance of the PEQ port. The shape of the PEQ port can be optimized for noise. A goal is to conserve the area of the port opening. As depicted, the opening shape may be an elongated oval.

Figure 5:
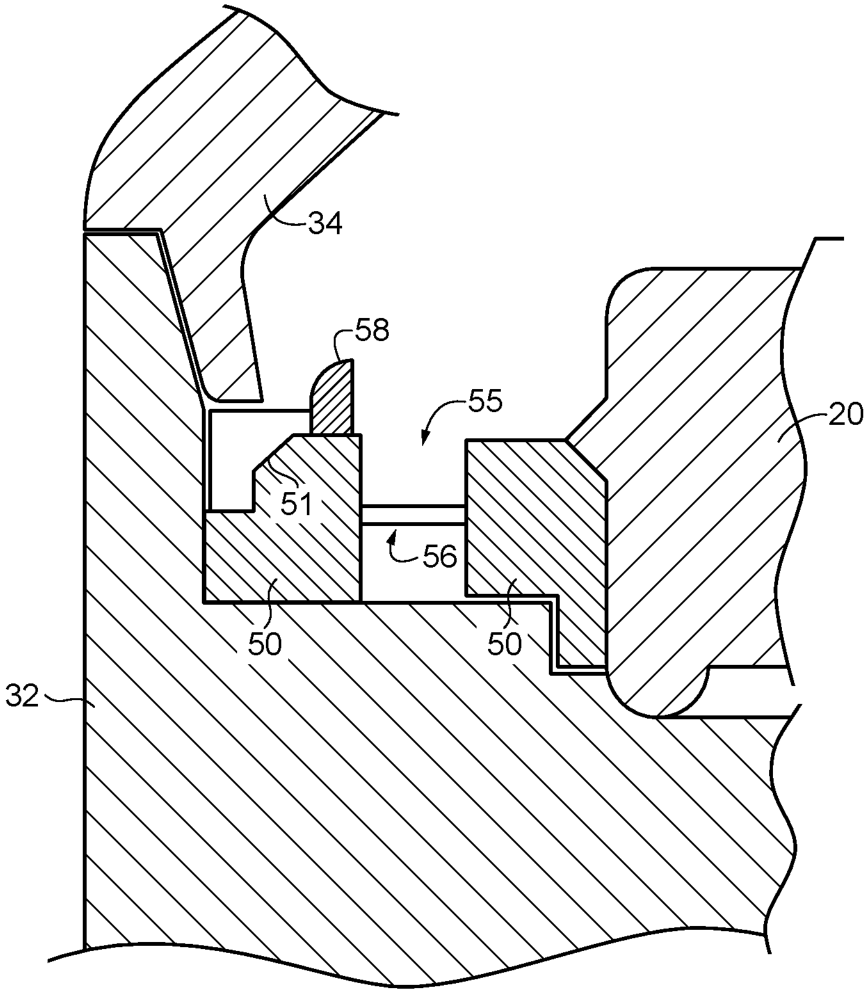
FIG. 5 is a partial cross-sectional view illustrating the frame and transducer of FIG. 4 mounted in the housing.

FIG. 5 is a schematic partial cross-section illustrating a manner in which frame 50 interfits with and is coupled to shells 32 and 34. Transducer 20 can be coupled to frame 50 with adhesive. Frame 50 can carry chamfer 51 that acts as a location at which frame 50 is glued to shell 32. Bead 58 can be located between chamfer 51 and PEQ 55, to prevent adhesive on chamfer 51 from being pushed into the PEQ port as the parts are assembled. Structure 56 with through-holes spans opening 55.

There are many possible through-hole arrangements and configurations. One is a configuration such as shown in FIG. 3, wherein structure with through-holes 56 includes a number of closely-spaced identical cylindrical through-holes. These through-holes can be arranged in an offset pattern (e.g., a honeycomb pattern) as shown, or can be arranged in other patterns such as circular. Generally, smaller holes are typically better for environmental resistance. An acoustically-resistive port can be accomplished with a structure with a number of through-holes, wherein the through-hole size and length, the number of holes, and the material of the structure dictate the acoustic resistivity. The holes can have a desired diameter and shape. One or both openings can be round, oval, or another shape. The holes can be tapered or flared, or not. The taper or flare can be at one end or both ends. The hole sizing and spacing can be designed to emulate the acoustic resistance of the typical mesh materials that are placed in ports in order to accomplish an acoustic resistivity. The resistance and inertance of the resistive element can be tuned by adjustment of the overall open area created by the holes, the pitch of the holes, the hole diameter, and the thickness of the structure with the holes (i.e., the lengths of the holes). Generally it can be desirable to have more smaller holes than fewer larger holes, as this can provide resistance with less inertance (acoustic mass). Also this can accomplish better contaminant ingress protection. However, there are practical limitations to the hole size that can be accomplished in injection molding. Generally but not necessarily, the hole diameters should not be less than their lengths. In one non-limiting example, a pattern of 200 micron holes with 200 micron inter-hole spacing can be used. More generally, the hole diameter and spacing can be the same. Or, it can be different. Another practical limitation arises from the small thickness of the port membrane which is perforated by these holes (i.e. the thickness of the material connecting the micro-openings). Traditional plastic injection molding involves a relatively viscous and high temperature thermoplastic being forced into a molding cavity at extremely high pressure. It is common to see pressures of 20,000 PSI in the molten plastic as it is forced to take the shape of the mold cavity. In the established field of "thin-wall molding" (sub-0.5 mm wall thickness) pressures may be even higher, which can lead to premature failure of mold components, especially those which are thin or unsupported. To enable the plastic to fill such thin wall sections without excessive pressure, as may be needed in some of the examples presented here, the viscosity of the plastic can be reduced. Use of liquid-crystal polymer (LCP) molding, and liquid injection molding (LIM) are examples of injection molding processes and materials that may be used here. When we refer to injection molding throughout this document, it includes these specialized techniques.

Figure 6A:
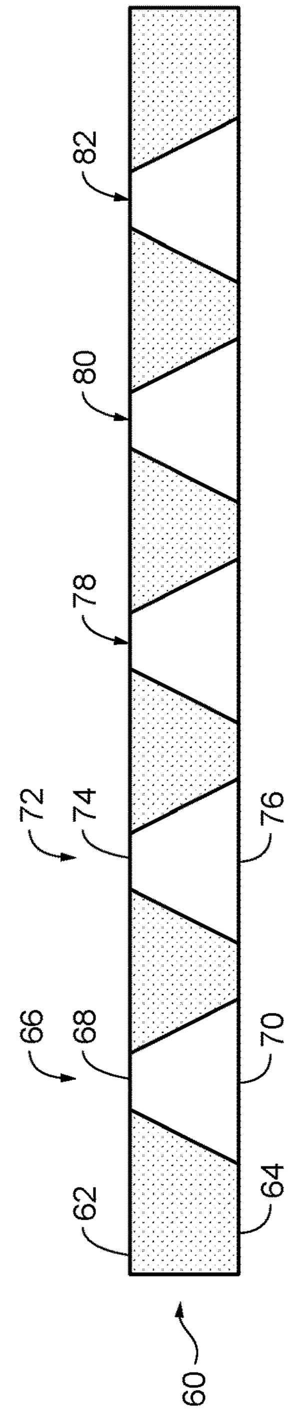
FIGS. 6A-6C are partial schematic cross-sectional views of three configurations of through-holes that can be used in a port.
Figure 6B:
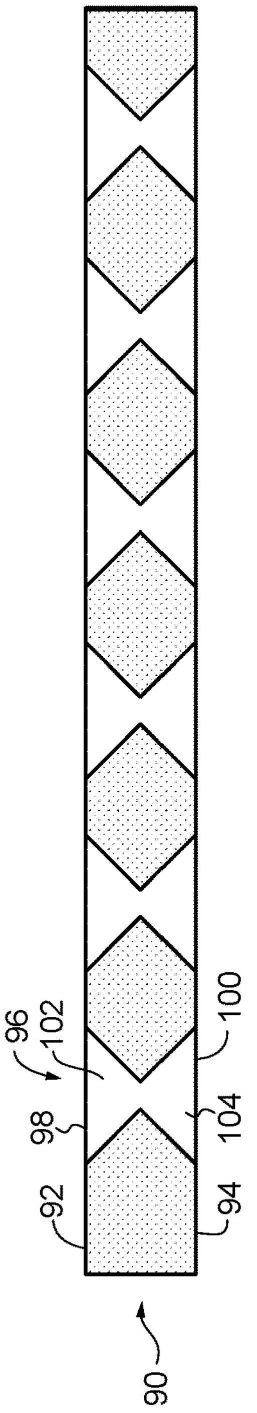
Figure 6C:
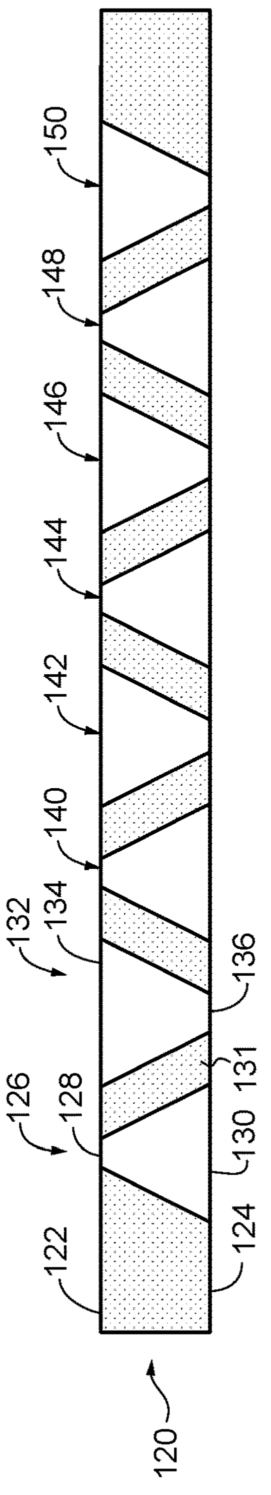

FIGS. 6A-6C illustrate three of numerous possible additional through-hole arrangements and configurations. In each of these cases each resistive element (i.e., through-hole) can be optimized by tailoring its cross-section at one or more heights along the length of the hole. This can help achieve a desired performance, such as water or particle ingress protection and/or acoustic performance. One way to achieve smaller hole size is to taper the holes as shown in FIG. 6A. Holes 66, 72, 74, 78, 80, and 82 are tapered such that their openings at surface 62 of structure 60 (e.g., openings 68 and 74 of holes 66 and 72) are smaller than their openings at opposed surface 64 (e.g., openings 70 and 76). Tapered openings can be formed with tapered pins on one side of the mold tool. The standing protrusions in the tool which form these openings (e.g., holes 66, 72, 74, 78, 80, and 82) are attached within the half of the mold tool which forms surface 64, in accordance with standard draft angle practices. The smaller openings on surface 62 are then formed by the "shut-off" created by the distal ends of these pins against the mating half of the mold tool (that half which forms surface 62). It is understood that there are standard techniques in the field of tool design which can be exercised at a toolmaker's discretion without fundamentally changing the resulting molded part. Examples of these techniques include but are not limited to: selection of varied materials and alloys in all components of the tool; use of interlock(s) at the end of the pins (whereby the steel that forms the hole may protrude past the tool surface which forms surface 62, locating into a recess in that surface); and the use of inserts, either static or "floating" within their parent half of the tool, which may encompass individual pins or a grouping of pins. All of these tool design techniques support manufacture of the part. One possible issue with this hole pattern is that there is more open area on one side (side 64) of wall 60 than on the other side (side 62) and so air can flow more easily in one direction than the other. This might cause DC pressure to build up on one side of the wall in an oscillating flow, which might have an effect on acoustic performance. One possible solution to these issues is the pattern in FIG. 6B, wherein there would be tapered pins on each side of the mold to create tapered holes but with the same size openings at each surface. For example, through-hole 96 has opening 98 at side 92 of wall 90, and the same size opening 100 at side 94 of wall 90. Each of volumes 102 and 104 is internally tapered. A possible issue with this pattern is that a series of small tapered pins in both of the mold halves have to meet exactly on center when the mold closes, which requires a high level of precision in the mold tool. The same result (i.e., the same amount of open area on each face of the wall) can be accomplished with the pattern shown in FIG. 6C, with hole tapers that run in both directions in different (e.g., alternating) holes. For example, through-hole 126 has small opening 128 on face 122 of wall 120 while it has a larger opening 130 on opposed wall face 124. Adjacent hole 132 has larger opening 134 on face 122 and smaller opening 136 on face 124. Holes 140, 142, 144, 146, 148, and 150 are also shown. Each hole can be created by identical tapered pins on each side of the mold, but the pins do not have to meet. Also, it may be possible to increase hole density with this pattern because the wall regions between holes (e.g., region 131 between holes 126 and 132) are uniform (i.e., the walls of adjacent holes are parallel) and may be made thinner than shown.

A number of implementations have been described. Nevertheless, it will be understood that additional modifications may be made without departing from the scope of the inventive concepts described herein, and, accordingly, other examples are within the scope of the following claims.

What is claimed is:

1. An earphone, comprising:
a first acoustic cavity;
an electro-acoustic transducer configured to deliver acoustic energy into the first acoustic cavity; and
a port that acoustically couples the first acoustic cavity to a different volume, wherein the port comprises a series of through-holes that are open to the first acoustic cavity and the different volume, wherein the port and the through-holes are defined by the same material.

2. The earphone of claim 1, further comprising a second acoustic cavity, wherein the electro-acoustic transducer is configured to deliver acoustic energy into the first and second acoustic cavities.

3. The earphone of claim 2, wherein the port directly acoustically couples the first and second acoustic cavities.

4. The earphone of claim 3, further comprising a frame that supports the transducer, wherein the port is integrated into the frame.

5. The earphone of claim 4, wherein the frame comprises an annular seat for the transducer, and an integral extension that comprises the port.

6. The earphone of claim 1, wherein the port comprises an integral structure that comprises the series of through-holes.

7. The earphone of claim 1, wherein the port comprises an acoustically resistive element.

8. The earphone of claim 1, wherein the port comprises an acoustically reactive element.

9. The earphone of claim 8, wherein the port comprises a tube.

10. The earphone of claim 1, wherein the port acoustically couples the first acoustic cavity to an environment external to the earphone.

11. The earphone of claim 10, wherein the port comprises a nozzle that is configured to directly deliver acoustic energy into an ear canal.

12. The earphone of claim 1, wherein the series of through-holes comprises a moisture-resistant element.

13. The earphone of claim 1, wherein the series of through-holes are created by molding, machining, laser drilling, chemical etching, electrical discharge machining, or electroforming.

14. The earphone of claim 1, wherein the through-holes of the series of through-holes are identical.

15. The earphone of claim 1, wherein the through-holes of the series of through-holes have lengths and diameters, and wherein the diameters of at least some of the through-holes vary along their lengths.

16. The earphone of claim 1, wherein the through-holes of the series of through-holes have lengths, and wherein at least some of the through-holes are tapered along their lengths.

17. The earphone of claim 16, wherein the through-holes of the series of through-holes have first openings that are open to the first acoustic cavity and second openings that are open to the different volume, and wherein some of the through holes have larger first openings than second openings, and some of the through holes have smaller first openings than second openings.

18. The earphone of claim 17, wherein the through holes have sidewalls, and wherein the sidewalls of adjacent through-holes are parallel.

* * * * *